United States Patent
Snelders et al.

(10) Patent No.: US 10,533,964 B2
(45) Date of Patent: Jan. 14, 2020

(54) GAS SENSOR ARRAY AND METHOD

(71) Applicant: Nederlandse Organisatie voor toegepast-natuurwetenschappelijk onderzoek TNO, The Hague (NL)

(72) Inventors: Dennis Johannes Maria Snelders, The Hague (NL); Arjen Boersma, The Hague (NL); Adriaan Jan de Jong, The Hague (NL)

(73) Assignee: Nederlandse Organisatie TNO, The Hague (NL)

( * ) Notice: Subject to any disclaimer, the term of this patent is extended or adjusted under 35 U.S.C. 154(b) by 371 days.

(21) Appl. No.: 15/322,344

(22) PCT Filed: Jun. 29, 2015

(86) PCT No.: PCT/NL2015/050474
§ 371 (c)(1),
(2) Date: Dec. 27, 2016

(87) PCT Pub. No.: WO2016/003272
PCT Pub. Date: Jan. 7, 2016

(65) Prior Publication Data
US 2017/0184531 A1    Jun. 29, 2017

(30) Foreign Application Priority Data
Jun. 30, 2014 (EP) ...................... 1417491

(51) Int. Cl.
*G01N 27/22* (2006.01)
*G01N 33/22* (2006.01)

(52) U.S. Cl.
CPC ......... *G01N 27/221* (2013.01); *G01N 33/225* (2013.01); *G01N 2027/222* (2013.01)

(58) Field of Classification Search
CPC ............... G01N 27/221; G01N 33/225; G01N 2027/222
(Continued)

(56) References Cited

U.S. PATENT DOCUMENTS 4,845,976 A * 7/1989 Johnson ............... G01N 27/221
                                                                          73/23.2
5,153,837 A * 10/1992 Shaffer ............... G06Q 50/06
                                                                          705/412
(Continued)

FOREIGN PATENT DOCUMENTS

WO          199908105       2/1999

OTHER PUBLICATIONS

Goodman et al.; Techniques and Systems for Analyte Detection; 1999, WO 99/08105 (Year: 1999).*

(Continued)

*Primary Examiner* — Farhana A Hoque
(74) *Attorney, Agent, or Firm* — OspreyIP, pllc; James R. Cartiglia

(57) ABSTRACT

The invention relates to a method for analyzing the composition of a gaseous stream comprising at least two gaseous components, one of which is methane; and to a sensor array and a gas sensor comprising such sensor array. The method comprises contacting the gaseous mixture with a sensor, wherein the sensor comprises a sensor array comprising at least two sensor elements, wherein each of said sensor elements comprises a transducer coated with a coating comprising a polymeric material having at least one property that is responsive to one or more of said gaseous components when exposed thereto, wherein said sensor elements differ at least in the composition of the coating, providing an energy input to said transducers that is converted to output signals based on said property, and obtaining said output signals.

21 Claims, 1 Drawing Sheet

Figure 1:
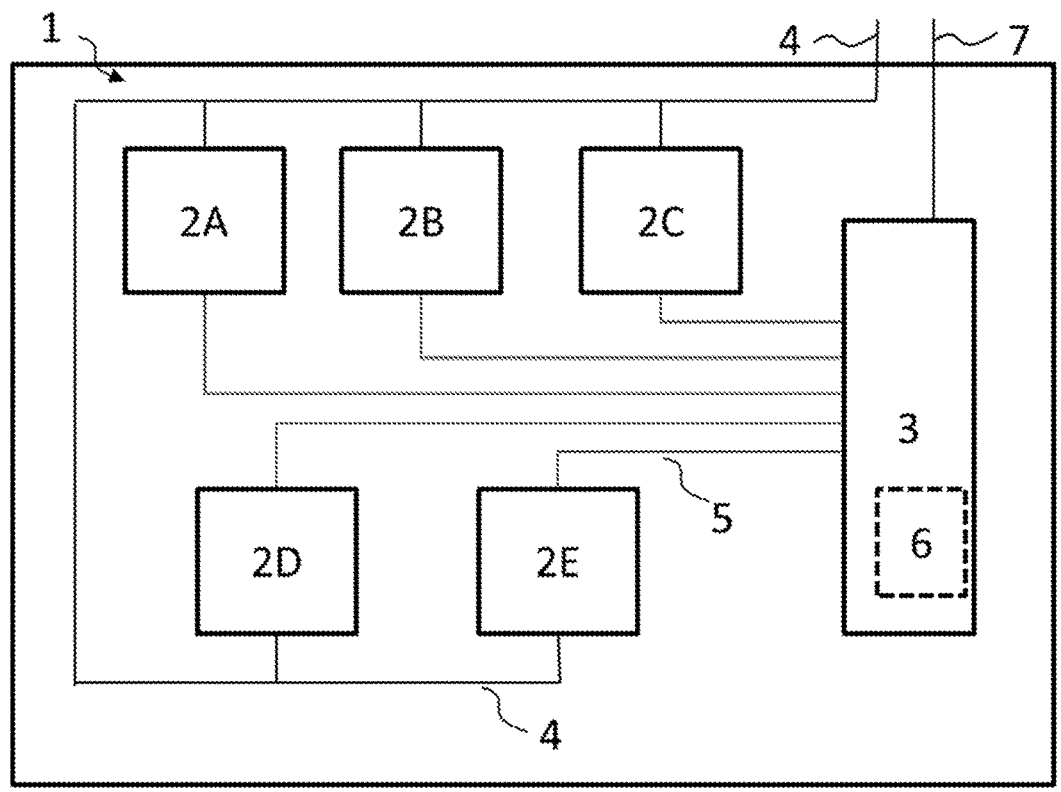

(58) Field of Classification Search
USPC .................................................. 324/663, 71.1
See application file for complete search history.

(56) References Cited

U.S. PATENT DOCUMENTS

| | | |
|---|---|---|
| 5,767,687 A | 6/1998 | Geist |
| 2004/0112764 A1 | 6/2004 | Stokes et al. |
| 2011/0316054 A1 | 12/2011 | Fedder et al. |

OTHER PUBLICATIONS

XP002728001 CN20071185465 Dec. 18, 2007 Dong et al.
Boulart, C., et al., "A novel, low-cost, high performance dissolved methane sensor for aqueous environments," Optics Express, Aug. 18, 2008. vol. 16, No. 17, pp. 12607-16217.
Khoshaman, A., et al., "Highly sensitive supra-molecular thin films for gravimetric detection of methane," Sensors and Actuators B 161 (2012) 954-960.

* cited by examiner

GAS SENSOR ARRAY AND METHOD

The invention relates to a method for analyzing the composition of a gaseous mixture comprising at least two gaseous components, one of which is methane; and to a sensor array and a gas sensor comprising such sensor array.

The transition to renewable and clean energy sources causes the composition of fuel gas (natural gas and biogas) in the gas grid to fluctuate more frequently and more severely. This increases the need for frequent, inline measurement of the gas composition, in particular of the calorific value. In addition, since biogas is typically produced at a larger number of smaller sites, the gas will be fed into the gas grid at numerous places. Therefore, the gas composition needs to be monitored at more points in the gas grid. Moreover, with a view to the fluctuations in the composition, industrial users often wish to monitor fuel gas streams for changes in the calorific value for dynamic control of processes running thereon. This can improve the energy efficiency and reduce carbon emissions of industrial processes that run on gas.

Accordingly, a need exists for sensors and methods for the real-time analysis of the composition of gas streams. Such sensors can in addition be used in advanced signalling systems, in smart fuel gas grids allowing for gas streams with varying compositions to be fed in, and for the smart mixing-in of other gases for specific applications. Such sensors are also desirable for purification and processing systems for biogas and synthesis gas. Another aspect is the future need to add hydrogen gas to fuel gas, because hydrogen gas can be used to store energy from fluctuating sustainable energy sources, in particular from solar energy and wind energy. Gas producers and hubs also need to measure carbohydrate content for tax reasons, to determine calorific value delivered to the grid, and for process control.

Current sensors for measuring the calorific value of natural gas and biogas streams are based on gas chromatography. Accordingly, these units are typically large, complex and expensive, since they comprise a sampling unit, a gas separation column and a detector. Moreover, they need storage containers for the carrier gas and the calibration gases. This makes the current sensors less suitable for use in the gas grid and at biogas plants. Other disadvantages include that they are not suitable for in-line measurement and have high equipment cost and high operating and maintenance costs. Other sensors are based on direct combustion calorimetry, which requires expensive and complex equipment. Still other sensors use infrared spectroscopy. These have the disadvantage that they are very sensitive to contamination, can not be miniaturized and have a low resolution between various hydrocarbons. The known commercially available instruments are considered to be too expensive for the desired monitoring of the gas composition at numerous points in the gas grid. For the long-term goal of the deployment of composition sensors in smart gas meters in households connected to the gas grid, a low price is critical.

Yet a further challenge is the transition from L-gas (e.g. from the Groningen field in The Netherlands) to H-gas (e.g. from Russia and Norway). This requires a broader operating range of any gas analyzer for use in the gas grid during and after the transition period. Accordingly, it is a requirement that the gas sensor can provide the desired accuracy (1% for the calorific value) for the gas streams GG (Groningen Gas), BioGas, HG (High calorific value gas) and FHG (Future HG) as defined herein.

Persaud (*Chem. Senses.* 1996, 21(5), 495-505) describes a conducting polymer odour sensor for agricultural malodour measurements. It mentions a strategy of sensing systems where individual elements in an array show broad, overlapping selectivity to chemical species.

A review of electronic nose technologies is given by Wilson et al. in *Sensors* 2009, 9, 5099-5148. They mention conducting polymer sensors that have resistance change as detection principle. These are not used for analysis of fuel gas. Disadvantages include the sensitivity to humidity and temperature, and limited sensor life.

Hagleitner et al. (*Nature* 2001, 414, 293-296) describe a single-chip gas sensor system based on sensitive polymeric layers of poly(ether urethane) on complementary metal-oxide silicon (CMOS) micro-transducers, including capacitive sensors.

U.S. Pat. No. 5,767,687 is in the field of humidity sensors relates to a condensable-vapour sensor of the surface capacitor type. The sensor is based on absorption of water vapour or other condensable vapours by a polymer film. An embodiment relates to a composite condensable-vapour sensor with a number of surface-type capacitive sensors that is said to display selectively among different vapours in mixtures of vapours and other gases. The document mentions arrays of sensors having different dielectric layers to distinguish among different vapour species. The document does not mention methane.

US-A-2004/0 112 764 relates to a multi-gas sensor device comprising catalytic metal gate-electrodes, wherein the sensor device is operates immersed in electrically non-conductive oil, for the detection of dissolved hydrocarbon gases in oil-filled electrical equipment. In an embodiment, an array of devices with different catalytic metals having different catalysis mechanisms to many gases can be used for simultaneous sensing of more than one gas species including methane. The document does not use polymeric materials in the coating.

An object of the present invention is to provide a method and a sensor array for analyzing the composition of a gaseous mixture, which addresses the above-mentioned problems at least in part.

It has surprisingly been found that this objective can be met by using responsive coatings in a sensor array. Some of the advantages of aspects of the invention include the mechanically simple construction, providing a sensor that can be simple, inexpensive and robust and has low costs. The sensor provides as advantage that it is suitable for continuous, in-line and/or real-time monitoring of parameters of the composition of gas streams, especially of the calorific value of fuel gas streams. Embodiments of the sensor have a high accuracy for the calorific value over a broad range of gas compositions. A further advantage is that the measurement does not affect the composition of the gas, unlike combustion based methods. The combined use of different sensor elements in an array provides as advantage that composition parameters can be measured with high accuracy even while each sensor elements individually has a lower selectivity.

Accordingly, the invention relates in a first aspect to method for analyzing the composition of a gaseous mixture, preferably a gaseous stream, comprising at least two gaseous components, one of which is methane, the method comprising contacting the gaseous mixture with a sensor, wherein the sensor comprises a sensor array comprising at least two sensor elements, wherein each of said sensor elements comprises a transducer coated with a coating comprising a polymeric material having at least one property that is responsive to one or more of said gaseous components when exposed thereto, wherein said sensor elements differ at least in the composition of the coating, providing an energy input to said transducers that is converted to output signals based on said property, and obtaining said output signals, wherein optionally said output signals are data signals.

The invention also relates to a sensor comprises a sensor array comprising at least two sensor elements, wherein each of said sensor elements comprises a transducer coated with a coating comprising a polymeric material having at least one property that is responsive to one or more gaseous components when exposed thereto, wherein said sensor elements differ at least in the composition of the coating. Preferably said one or more gaseous components include methane.

The term "array" refers to any combination of at least two elements that are spatially separated. In particular, the term "sensor array" refers to a combination of sensor elements, wherein the sensor elements are spatially separated and arranged such that each sensor element has a surface for exposure to the same gaseous atmosphere. The term "sensor" refers to the sensor array in combination with a casing or housing, and typically comprises components such as electronics, a processor, and/or a memory device. The casing preferably comprises a chamber to which the sensor elements are exposed and wherein said chamber is provided with at least one opening for a gas stream. The term "sensor element" refers to a transducer with the coating.

The term "coating" is used broadly to refer to any layer on the surface of a transducer, and includes for example a layer of discrete particles, a layer of a continuous material, and a layer comprising discrete particles in a layer of a continuous matrix material. The layer may have a complete or incomplete coverage of the surface of the transducer that forms the substrate.

The term "fuel gas" is used to denote a gaseous mixture comprising methane as main component by volume (e.g. at least 50 vol. %, preferably at least 60 vol. %). The term includes natural gas, biogas and combinations thereof. Although such streams are mostly used as fuel, they are defined herein by their composition and are not restricted to a particular use.

The term "measuring" or "determining" a property of a gas mixture as used herein, in particular of the calorific value, includes indirect measurement of such property by measuring a response of parts of a sensor to the gas mixture and calculating the calorific value based on this response.

The term "in-line" refers to an analyzer which is connected to a process or stream and conducts automatic sampling or does not need sampling and is based on continuous flow (either of the main stream or of a side stream).

The term "calorific value" refers to the amount of heat released during the combustion of a specified amount of the gas mixture. ISO 6976:1995 describes a standard method for the calculation of the calorific value, density, relative density and Wobbe index from the composition of a natural gas stream.

Cryptophane refers to compounds with molecules formed by two [1.1.1]-orthocyclophane units connected by three bridges. A review is provided in "Cryptophanes: Molecular Containers" in Atwood et al., *Encyclopedia of Supramolecular Chemistry*, CRC Press, 2004, pp. 340-348.

Hard polydimethylsiloxane (HPDMS) is well known in the art and can be prepared from trimethylsiloxyterminated vinylmethylsiloxane-dimethylsiloxane (VDT-731; Gelest) and methylhydrosiloxane-dimethylsiloxane (HMS-301; Gelest) copolymers, as described in Schmid et al. (*Macromolecules* 2000, 33, 3042).

The term "comprising" does not exclude the presence of any steps or elements other than those recited, and encompasses the variants "containing", "consisting essentially of" (for example "consisting for at least 50 wt. % or at least 90 wt. % of") and even "consisting of".

The phrase "copolymers of a polymer" is used to indicate copolymers comprising at least one of its monomers in common with that polymer, including block, alternating, linear and branched copolymers comprising at least one monomer in common with the polymer.

An aspect of the invention relates to a method for analyzing the composition of a gaseous mixture, preferably gaseous stream comprising at least two gaseous components, one of which is methane. Herein, analyzing refers to determining any composition parameter of the gaseous mixture, including the relative concentrations of one or more of said gaseous components. Optionally the method involves determining one or more properties of the total gaseous mixture (such as the calorific value), with or without an intermediate step of calculating the concentration of one or more particular components.

The sensor optionally measures in addition one or more properties of the gaseous mixture that are not related to its composition, such as, pressure and temperature, and the flow rate in case of a gaseous stream, and optionally comprises sensor elements for these properties. Such sensor elements are well-known in the art.

The gaseous mixture may comprise minor amounts of a liquid (typically less than 1 vol. %) or solid material (typically less than 0.1 wt. %), for example dust. The gaseous stream is typically transported by flowing through a pipeline or tube. The method may also comprise the measurement of properties of a non-flowing gaseous mixture (atmosphere), for example of a sample.

The method comprises contacting the gaseous mixture with at least parts of the sensor, in particular exposing the coatings of the sensor elements to the gas. Preferably, the method comprises continuously contacting a gaseous stream with the sensor array, in particular constant exposure of the polymeric material of the coating to the gas. For example, the method can comprises passing the gas stream over the sensor elements. This is for example useful for methods for determining the calorific value. Preferably, the gas is not diluted and preferably no carrier gas is used. Typically, the gas stream is passed over the sensor elements by convective flow, for example caused by the flow of the gas stream in a pipeline. The method optionally comprises a pre-treatment of the gas stream prior to contact with the sensor. For instance, the pre-treatment may involve removing at least some non-gaseous contaminations from the gas stream, such as droplets and particles. For instance, the method may comprise filtering to trap dust and droplets to prevent contamination of the sensor.

The sensor comprises a sensor array, which comprises at least two sensor elements, such as two, three, four, five, six or more sensor elements. Each of these sensor elements comprises a transducer coated with a coating comprising a polymeric material. The transducer and/or coating are independently selected for each of said elements, unless particular combinations are specified herein.

The coatings, preferably the polymeric materials of each of said coatings, have a property that is responsive to one or more of the gaseous components when exposed thereto. Preferably, the polymeric material is permeable to one or more of the gaseous components. Preferably exposure of the polymeric material to the gaseous components causes these to be sorbed by it, due to absorption and/or adsorption. The polymeric material is preferably at least in part amorphous, for example glassy or rubbery, or preferably at least not fully crystalline, and preferably comprises free volume in which gases can diffuse and be sorbed.

The polymeric material, or at least the coating, has at least one property that is responsive to one or more of said gaseous components when exposed thereto. Preferred properties include the complex dielectric constant, the conductivity, the complex refractive index, the density, the volume and the mass. Sorption of gas in the polymeric material and/or molecular encapsulation material can cause a change of one or more of these preferred properties of the coating. The property is typically measured for the coating, including sorbed components.

The coatings may comprise in addition materials which are not polymeric and which may or may not have a responsive property. In addition, the coatings may comprise materials that do not have a responsive property, which materials may be polymeric or not. Moreover, the sensor array may comprise sensor elements that are not coated with a polymeric coating, for example a temperature sensor element.

The sensor array comprises at least two sensor elements that differ at least in the composition of the coating. In addition, the sensor array may comprise sensor elements that are identical to each other, or that differ in some other aspect as the composition of the coating, such as the thickness or porosity of the coating or the type of transducer. In the at least two sensor elements, the coating composition can have a different polymeric material and/or have other components that differ, or they can differ in the relative amounts of at least one component of the coating. The at least two sensor elements can have the same or different responsive property. Preferably, the type of transducer, the responsive properties, the type of energy input and data signal is the same for the at least two sensor elements.

The transducer is generally configured for converting an energy input to an output signal, preferably a data signal. Suitable energy inputs include for example an electric current, an electromagnetic wave, an optical signal, and a vibration. The output signal is typically an electronic signal. The method comprises a step of providing an energy input to said transducers. The energy input is converted into output signals. An embodiment of the method may for instance involve providing an electric current to the transducer, such that data signals are obtained from the transducer as an electric signal, such as an analogous or digital signal.

The use of said coating comprising polymeric material and having said responsive property advantageously provides a simplified method of measuring the calorific value of a fuel gas stream. Based on modelling experiments that were carried out for GG, BioGas, HG and FHG gas streams, the insight was obtained that a sensor array can be used for measuring the calorific value over a broad range with sufficient accuracy, preferably with four to six types of sensor elements. It was found that the sensor array preferably has the following accuracies, in order to determine the calorific value with the desirable accuracy of 1% or less, for GG, BioGas, HG and FHG gas: a maximum error in methane detection of 1%, a maximum error in ethane detection of 5%, and/or a maximum error in propane detection of 50%.

Accordingly, this opens the new approach of using a sensor comprising a sensor array comprising different types of sensor elements that complement each other to obtain a cumulative accuracy that is sufficient for inline monitoring of the calorific value. Typically, each sensor element gives a signal (output signal) corresponding to the amount of gas sorbed in its coating. As the at least two sensor elements have a defined and different coating composition, these signals can be used to calculate composition parameters of the gas to which they are exposed, typically based on a pre-established correlation between these signals and the parameter.

Preferably, the gaseous mixture comprises, in addition to methane, one or more selected from the group consisting of ethane, propane, carbon dioxide and water. More preferably, the gas stream comprises natural gas or biogas. Preferably, the gaseous stream is a stream of natural gas or biogas or a mixture comprising natural gas and/or biogas. In case of natural gas, the gaseous stream typically comprises at least 70 vol. % methane, typically 80 vol. % or more, and 1-10 vol. % of total $C_2$ to $C_6$ alkane components, in particular ethane and propane. Natural gas typically comprises 0.2-20 vol. % $N_2$, and 0.5-5 vol. % $CO_2$. Biogas is rather different from natural gas and typically comprises 50-75 vol. % methane, 25-50 vol. % $CO_2$, 0-10 vol. % $N_2$, 0-1 vol. % $H_2$, 0-3 vol. % $H_2S$ and 0-1.0 vol. % other components. However, the methane concentration can be increased up to 95 vol. % by purifications. Preferably, the sensor of the invention is suitable for both natural gas and biogas. Preferably, the method is carried out at a temperature between −20° C. and 100° C., i.e. the gas to which polymeric material is exposed has a temperature in such range, in particular in case of natural gas or biogas. These temperatures distinguish from combustion based methods.

Preferably, the measurement does not alter the composition of the gas stream, preferably it does not involve chemical reactions resulting in the formation and release of chemical compounds from the sensor that were not in the gas stream prior to the measurement.

Preferably, the transducers are capacitive sensors and the responsive property of the coating, preferably the aid polymeric material is the relative permittivity (the dielectric permittivity of the material expressed as a ratio relative to the permittivity of vacuum), for at least some of the sensors, more preferably for each of the sensor having the coating.

A preferred capacitive sensor transducer can measure a change in the relative permittivity (dielectric constant) of the coating, for example caused by absorption of one or more gases. Capacitive sensors are well known as such. Preferably the capacitive sensor comprises an electrically insulating substrate, a pair of interdigitated electrodes or spiral electrodes positioned on said electrically insulating substrate, and a dielectric layer as coating at least on substrate parts between and/or on said electrodes. A highly preferred capacitive sensor has a comb structure. Such sensor for instance can comprise two electrodes that are deposited on a substrate, wherein the electrodes have comb-like extensions that are spaced apart on the substrate, wherein at least substrate parts between comb-like extensions are coated. A suitable capacitance sensor is for example AD7746 from Analog Devices. Suitable bare comb electrodes are generally available. The capacitance is preferably measured at a frequency between 0.1 Hz and 1 MHz or preferably by the detection of a relaxation time using a single pulse. For capacitive sensor transducers, the relative permittivity of the coating changes as a function of the partial pressure of the absorbent in the gaseous stream. The change in capacitance is influenced typically by the change in dielectric constant and by the swelling of the coating caused by absorption of the gaseous component. Based on detailed calculations of the effect of the thickness on the change in capacitance due to absorption of gas, it was found that the highest sensitivity is obtained with the preferred thickness of the coating of 0.1-7 µm, more preferably 0.5-5 µm, or 1-3 µm, even more preferably 1.5-2.5 µm, preferably in combination with a sensor active area of 0.5-2 mm$^2$ for each sensor element. This allows for miniaturisation and high sensitivity.

Another suitable transducer is for example based on a piezoelectric MEMS (microelectromechanical systems) resonator and CMOS (complementary metal-oxide-semiconductor) oscillator readout. An exemplary implementation is given in Petrescu et al. "Power-Efficient Readout Circuit for Miniaturized Electronic Nose", Proceed. 2012 IEEE International Solid-State Circuits Conference; incorporated herein by reference. A micro beam lithographed into a Si chip acts as mechanical resonator and is provided with an absorptive coating and a piezoelectric element for stimulation and read-out. In presence of the probe gas, the coating expands and alters its mass and the tensile/compressive forces in the Si-beam, which accordingly has a shifted resonance frequency.

A further suitable transducer is a Quartz Crystal Microbalance (QCM). A QCM measures a mass per unit area by measuring the change in frequency of a quartz crystal resonator. The resonance is disturbed by the addition or removal of a small mass due to sorption of one or more gases in the coating, the sorption of the gases is typically reversible. The QCM can for instance comprise a thin piezoelectric plate with electrodes on both sides. Due to the piezo-effect, an alternating current voltage across the electrodes induces a shear deformation and vice versa. The electromechanical coupling provides a simple way to detect an acoustic resonance by electrical means. An overview of QCM is given in Vashist et al. (*Journal of Sensors* 2011, Article 571405).

Other possible transducer include fibre Bragg gratings, optical micro-ring resonators, and electrodes for conductivity/resistance readout.

The method preferably comprises further processing of the obtained output signals. Accordingly, the method preferably further comprises:
  providing said output signals to a computer processor which is in communication with a computer memory device in which instructions are stored for conversion of said output signals to an estimated composition parameter, and
  calculating in said processor said estimated composition parameter using said instructions and said output signals from said different sensor elements.

In such preferred method, the output signals from the individual sensor elements are combined at least in a computer processor and the method preferably comprises a calculation of a composition parameter based on the combined output signals of different sensor elements of the sensor array.

Optionally, the sensor comprises a data acquisition system as is conventional, for example comprising signal conditioning circuitry to convert sensor (output) signals into a form that can be converted to digital values, and analogue-to-digital converters, which convert conditioned sensor signals to digital values. Such digital output signal can be used for calculations.

Suitable computer memory devices include for example EEPROM (Electrically Erasable Programmable Read-Only Memory), flash, and a hard disk. Suitable processors include all types of microprocessors, such as a microcontroller and a CPU.

The computer processor is in communication with the transducer and typically stores values of the output signal in a computer memory. For example, the stored values are read by the processor with some frequency. For instance, the values can be used to calculate a calorific value and/or one or more other properties of the gas stream, for instance according to a schedule or at certain intervals. The processor is accordingly typically adapted, programmed and/or configured for calculating a calorific value and/or one or more other composition parameters of the gas stream using the output signals from the transducer. Preferably, each sensor element is connected to a sensor interface circuit, which transports the signals from the sensor array to a processor. The processor which calculates the composition parameters can be connected to the sensor array for example wired, wireless or through a network such as the internet.

Preferably, the method is a method of determining the calorific value of the gaseous stream. In that case, the method preferably comprises these steps, and the composition parameter is the estimated calorific value. The method may for example comprise using the estimated calorific value for financial settlement for gas delivery or for dynamic control of a downstream process. The method may comprise calculation of a plurality of estimated composition parameters. Preferably, the method is for determining the methane concentration, preferably in combination in combination with the concentration of ethane and of propane, more preferably in combination with determining the concentration of one or more of $CO_2$ and $N_2$ and optionally the relative humidity. The method preferably comprises calculating the estimated values of the concentrations. The instructions or algorithm can be based on an experimentally determined response matrix for the object gases or property at issue.

Preferably, the method is a method of in-line analysis of the composition of the gaseous stream, preferably for determining the calorific value. The sensor is accordingly preferably an in-line device mountable or mounted to, or integrated in a pipeline segment or flow meter. In that case preferably the step of contacting the gaseous stream with said sensor comprises flowing at least part of the gaseous stream over the sensor array.

Preferably, the sensor is capable of operating at least in a part of the range of −20° C. to 55° C., more preferably at least in the range of −20° C. to 70° C., and preferably at least in a part of the range of 1-10 bar absolute, which is typical for the gas grid. The method of the invention can for example be carried under these conditions. In a preferred embodiment the method is carried out at a temperature and pressure at which methane, preferably also ethane and $CO_2$, are not condensable. The sensor is preferably adapted for operating on gas streams having a flow of from about 1 l/min (such as in household environments), or up to 1000 m$^3$/h or even 10 000 m$^3$/h (such as in distribution networks). Some preferred embodiments of the gas sensor are resistant to gas streams with up to 5 mg $H_2S$/Nm$^3$, up to 1 mol % aromatic hydrocarbons, up to 5 ppm by volume siloxanes, and/or total sulphur up to 45 mg/Nm$^3$. The person skilled in the art of sensor for natural gas streams is familiar with materials that are resistant to these conditions. The sensor preferably has a power consumption of less than 1 W, more preferably less than 1 mW for battery driven devices. The sensor preferably has a footprint within 2 cm×2 cm, and preferably fits in a sensor body of 2 cm×2 cm×2 cm. In in-line devices any electronics are preferably contained within the casing and sealed off from a fuel gas stream for better safety.

The sensor array may be constructed in various ways. A plurality of sensors elements may be formed on a single (silicon) substrate, for example a chip provided with two or more sensor elements. In addition, the sensor array may be formed as separate discrete elements on a printed circuit board, each comprising one or more sensor elements in the form of one or more coated transducers. Alternatively, the sensor array may be provided on two or more printed circuit boards (PCB), each PCB comprising one or more sensor elements and each having a data connection to a common data processor. Each sensor element preferably comprises an exposed surface of the coating of at least 0.010 mm$^2$, or at least 0.10 mm$^2$, more preferably at least 1.0 mm$^2$, even more preferably at least 2 mm$^2$, typically less than 50 mm$^2$. The sensor elements are typically spaced apart at sufficient distance such that they do not disturb each other, typically at by at least 0.10 mm, preferably at least 1.0 mm, typically by an air gap.

Some preferred sensor arrays will be described. Aspects of the invention relate to embodiments of the method of the invention using these sensor arrays and to these senor arrays as such. The sensor array as such is not restricted to any particular use or gaseous stream. The sensor array of an aspect of the invention can be further characterized independently by the chemical composition of the coatings, the functional properties of the coating materials such as absorption selectivity, or its configuration for inline analysis of gas streams, or a combination thereof.

In an aspect, the sensor array comprises at least two sensor elements, which have different coatings. Preferably, the sensor array comprises sensor elements with one or more of the following coatings: a coating comprising a molecular encapsulation material, a polar coating in combination with an apolar coating on a different sensor element, and optionally a coating that can form hydrogen, polar and/or covalent bonds with $CO_2$.

Herein, molecular encapsulation materials include Metal Organic Frameworks (MOFs), zeolites and molecular cage compounds such as cryptophane. The molecular encapsulation material may also include organic supramolecular compounds, or molecular containers, for instance hemicarcerands. The molecular encapsulation material has a structure with cavities and/or pores through which at least some gases can enter and exit. Molecular encapsulation materials are preferably included in a coating which also comprises a polymer, for example a polymeric organosilicon compound. The polymer may form a polymeric matrix. Preferably, the molecular encapsulation material is for example applied in an amount of at least 1% based on weight of the material and polymer in the coating together, or at least 5%, usually less than 75%.

An aspect of the invention relates to a sensor array which is preferred for the method of the invention, wherein the coating of at least one sensor element comprises a compound with selectivity for absorption of methane over ethane, and the coating of at least one other sensor element comprises a compound with selectivity for absorption of ethane and/or propane over methane. This is in particular preferred in case the method is for determining the calorific value of the gaseous mixture and for gaseous mixtures further comprising ethane and/or propane. For example, the sensor element can have a stronger response of said responsive property for the gas for which the compound has selectivity over said other gas. Selectivity for absorption is used to refer to sorption including adsorption. For instance, the amount sorbed (cm$^3$ gas/g compound) is higher at eqeual pressure and temperature, e.g. 1 bar and 20° C.

Some examples of the suitable compounds include cryptophane compounds for methane selectivity and PDMS, MOFs and zeolites for ethane and/or propane selectivity, in addition to the other suitable compounds described herein. PDMS is an apolar rubbery polymer with relatively large pores (on a molecular scale).

Preferably, each of the transducers of said sensor elements in said sensor array is a capacitive sensor.

In an aspect, the sensor array is characterized by a combination of coating materials. The coatings preferably comprise one or more selected from polymeric materials, clays and molecular encapsulation materials such as cage molecules, zeolites, metal organic frameworks. These compounds can provide good selectivity for the components of a fuel gas stream.

Suitable polymers include natural and synthetic polymers and polymers having a carbon based backbone and/or having an inorganic backbone, and combinations thereof.

If used, a molecular encapsulation material, such as zeolite, MOFs or cryptophane compound, is preferably applied as coating in a mixture with a polymer in an amount of at least 1 wt. %, or at least 10 wt. %, or at least 20 wt. %, typically less than 60 wt. % of the coating material.

Preferred cage molecules are cryptophane compounds, in particular cryptophane-A. The cage volume of cryptophane A matches the size of methane and it has a selective interaction with methane that leads to slow release thereof. Cryptophane A provides as advantage, that ethane and propane interference is low until 8 vol. %. The coating can be prepared for example from a solution in THF or by mixing in a polymer matrix and coating from a solution thereof. As shown in US-A-2004/0 062 715, some example cryptophane compounds have the formula I, wherein n=2 for cryptophane-A or n=3 for cryptophane-E.

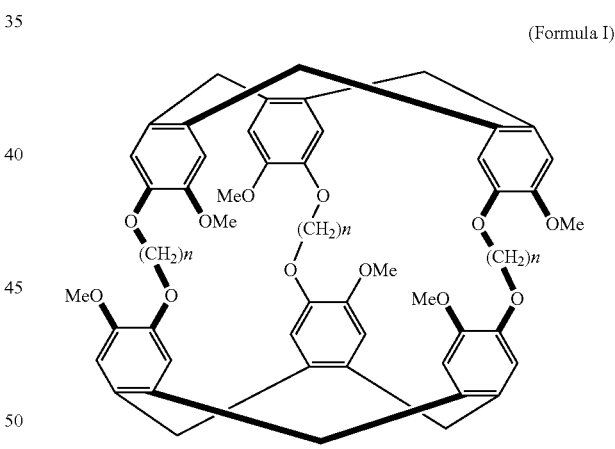

(Formula I)

Possible metal organic framework (MOF) materials for use in one or more of the coatings includes: MOF CAU-1 (having the formula $[Al_4(OH)_2(OCH_3)_4(H_2N\text{-}bdc)_3]\cdot xH_2O$); MOF UTSA 33a (having the formula $Zn_4O(FMA)_3$), Mg-MOF-74 (Linker: 2,5-dihydroxyterephthalic acid, metal source: Mg salts), Basolite® C300 and an organophilic zinc MOF with zeolitic framework such as Basolite® Z1200. For instance, a MOF with 2-methylimidazole as linker, preferably with zinc salts as metal source, for example with a pore volume of 0.630-0.640 cm$^3$/g, such as ZIF-8 (Basolite® Z1200 available from Sigma-Aldrich®)

Possible zeolites include: zeolites with ISV structure, such as ITQ-7, with MOR structure, such as Mordenite, with MFI structure, such as ZSM-5 or silicalite or CZP 200 available from Clariant, optionally in $NH_4$ form; with FAU structure, such as zeolite X (Ca and Na form), with LTA structure, such as zeolite A (K form and Na form) and macro porous titanosilicates zeolites (ETS), including Na-ETS-10, Ba-ETS-10, Ba/H-ETS-10, which are all well known in the field of zeolites. The zeolites and MOF materials are useful for selectivity of components of fuel gas streams, based on in particular size exclusion and polarity. Zeolites can allow for discrimination of molecules by size and structure.

Preferred clays include smectite, including bentonite and montmorillonites, such as Intercalated Wyoming clay, for example Al pillared and Zr pillared Intercalated Wyoming clay. Clays are useful for selectivity of components of fuel gas stream based on the size distribution of the pores of the clay, in particular they can have a higher affinity for ethane and carbon dioxide than for methane. These MOF materials, zeolites and clays can for instance each be combined with polymers as matrix.

Preferably, at least one sensor element has a coating comprising a cryptophane compound and/or one or more polymers selected from the group consisting of a polymer comprising repeating units comprising an amine group, a fluoropolymer, a polymeric organosilicon, a polyisoprene, a polymer of intrinsic microporosity, and a cured epoxy resin. More preferably, the sensor array comprises two, more preferably three or four sensor elements, each of said sensor elements comprising a different one selected from the group consisting of a polymer comprising repeating units comprising an amine group, a fluoropolymer, a polymeric organosilicon, and a cured epoxy resin. For example, a sensor array may comprise two, three, at least four, or at least six sensor elements, each having a different coating, wherein the polymers of said coating are selected from the group consisting of a fluoropolymer, a polymeric organosilicon, and a cured epoxy resin, wherein said sensor array comprises at least two sensor elements comprising cryptophane, metal organic framework, or zeolites.

Polymers comprising repeating units comprising an amine group have advantageous high selectivity for $CO_2$ as they can form carbamate species. Examples of suitable polymers comprising repeating units comprising an amine group are polyallylamine (PAAm) and polyethyleneimine (PEI; also known as poly(iminoethylene)), and copolymers thereof.

Fluoropolymers include any polymers comprising fluoro groups, preferably fluorocarbon based polymers are used, preferably a homopolymer or copolymer of at least fluorine comprising monomers. Suitable fluoropolymers include polytetrafluoroethylene (PTFE, Teflon® available from DuPont), and copolymers thereof, such as a copolymer of tetrafluoroethylene and 2,2-bis(trifluoromethyl)-4,5-difluoro-1,3-dioxole (Teflon® AF), preferably in amorphous form. Further suitable fluoropolymers include fluorinated ethylene propylene (FEP), perfluoroalkoxy alkane (PFA) and polyvinylidene fluoride (PVDF), and copolymers of any of these. The selectivity is typically based on the free volume. Fluoropolymers may advantageous provide selectivity to $CO_2$, in particular apolar glassy fluoropolymers, because of the low permeability for larger molecules, such as ethane and propane.

Organosilicon polymers, also known as silicone materials, include polymerized siloxanes or polysiloxanes, preferably silicones are used which are polymers with the chemical formula $[R_2SiO]_n$, where R is an independently selected substituted or substituted organic group, such as methyl, ethyl, or phenyl; and copolymers thereof. Preferred polysiloxanes comprise an inorganic silicon-oxygen backbone (—Si—O—Si—O—Si—O—) with organic side groups attached to the silicon atoms.

Polyisoprene compounds can also be used in said coatings and for example include polymers and copolymers of isoprene, including poly-cis-isoprene and copolymers with styrene or isobutylene.

A polymer of intrinsic microporosity (PIM) is in particular any amorphous, glassy polymer that contains interconnected pores of less than 2 nm diameter, which pores preferably arise directly from the shape and rigidity of the component macromolecules.

Preferably, the sensor comprises at least one sensor element that has a coating comprising one or more polymers selected from:
  a fluoropolymer selected from the group consisting of polymers and copolymers of tetrafluoroethylene, such as PTFE, FEP (fluorinated ethylene propylene), PFA and MFA (copolymers with perfluoroethers), and polymers and copolymers of vinylidene fluoride (PVDF), more preferably copolymers of tetrafluoroethylene and 2,2-bis(trifluoromethyl)-4,5-difluoro-1,3-dioxole (Teflon® AF),
  a polymeric organosilicon compound selected from the group consisting of polydimethylsiloxane (PDMS), polydiethylsiloxane, polydiphenylsiloxane, preferably PDMS, and copolymers of any of these polymers, more preferably linear and/or cross-linked PDMS,
  a cured epoxy resin selected from the group consisting of cured cycloaliphatic epoxides and aromatic epoxides, preferably a cured epoxy resin comprising a cross-linked polymer comprising aromatic rings,
  an amine comprising polymer selected from the group consisting of polyallylamine (PAAM), polyvinylamine, polyethyleneimine, and copolymers of any of these polymers.

More preferably, the sensor array comprises two, three or four sensor elements, each of said sensor elements comprising a polymer selected from a different one of said four groups of polymers. Preferably, the sensor array comprises three sensor elements selected from said group of fluoropolymer, group of polymeric organosilicon compound, and group of cured epoxy resin.

Preferably, the sensor array comprises the combination of: a first sensor element comprising a coating comprising a zeolite, a metal organic framework, and/or a polymer comprising repeating units comprising an amine group, a second element sensor comprising a coating comprising a fluoropolymer, a third sensor element comprising a polymeric organosilicon compound, wherein said sensor elements are different from each other. Preferably, the coating of at least one sensor element of the sensor array preferably comprises a coating comprising a cryptophane compound and a polymer, wherein the polymer is preferably a polymeric matrix for said crypthophane. Preferred is crypthophane A. Preferably, that coating comprises cryptophane compounds in an amount of 0.1-60 wt. %, such as 1-10 wt. %, for example 1-5 wt. %, based on total coating composition. Optionally, the sensor comprises a fourth sensor element comprising a cured epoxy resin. The sensor element comprising a cryptophane compound is preferably a fifth sensor element different from the first to third and optional fourth sensor element, and the polymer of the cryptophane comprising sensor element can be any kind of polymeric material, including the polymers specified for first to third sensor element. Optionally the sensor array comprises one or more yet further sensor elements, such as a sixth sensor element. Preferably, the sixth sensor element comprises a coating comprising a zeolite or a metal organic framework. For instance, a sixth sensor element may comprise a coating comprising a zeolite, for example in case the first sensor element comprises a coating comprising a metal organic framework. The zeolite, metal organic framework, or a polymer comprising repeating units comprising an amine group are optionally used independently of each other or in combination. A polymeric organosilicon compound is preferred as polymeric matrix. Typically, the coatings of the first to third sensor element comprise at least 90 wt. % of the indicated polymers. The coatings are typically in the form of a continuous layer of these polymers. These preferred combinations of coating materials were found to give good accuracy for measuring the calorific value of natural gas.

Preferably, the sensor array further comprises a fourth sensor element comprising a coating comprising a cured epoxy resin, preferably wherein said cured epoxy resin is a cross-linked polymer comprising aromatic rings, more preferably cured SU-8 epoxy resin. SU-8 resin is available from Microchem and Gersteltec.

In a preferred embodiment, the sensor array comprises:
a first sensor element comprising a coating comprising poly(allylamine),
a second sensor element comprising a coating comprising a homopolymer or copolymer of tetrafluoroethylene, preferably a copolymer of tetrafluoroethylene and 2,2-bis(trifluoromethyl)-4,5-difluoro-1,3-dioxole,
a third sensor element comprising a coating comprising cured polyepoxide SU-8 resin giving a polymer comprising bisphenol-A diglicydyl ether residues,
a fourth sensor element comprising a coating comprising hard polydimethylsiloxane and a cryptophane compound in a 90:10 to 99.5:0.5 mass ratio, and
a fifth sensor element comprising a coating comprising hard polydimethylsiloxane, or polydimethylsiloxane and a cryptophane compound, preferably in a 50:50 to 95:5 mass ratio;
wherein each of said first to fifth sensor element preferably has a capacitive sensors as transducer.

In another preferred embodiment, the sensor array comprises:
a first sensor element comprising a coating comprising a polymer and a metal organic framework compound,
a second sensor element comprising a coating comprising a homopolymer or copolymer of tetrafluoroethylene, preferably a copolymer of tetrafluoroethylene and 2,2-bis(trifluoromethyl)-4,5-difluoro-1,3-dioxole,
a third sensor element comprising a coating comprising cured polyepoxide resin, preferably SU-8 resin giving a polymer comprising bisphenol-A diglicydyl ether residues,
a fourth sensor element comprising a coating comprising polydimethylsiloxane,
a fifth sensor element comprising a coating comprising polydimethylsiloxane, and a cryptophane compound, preferably in a 50:50 to 95:5 mass ratio, and
a sixth sensor element comprising a coating comprising a polymer and a zeolite,
wherein each of said first to sixth sensor element preferably has a capacitive sensors as transducer.

Typically, the coating of the first to fifth or sixth sensor elements consists of these compounds, preferably in the form of a continuous layer over the transducer as substrate. This combination of coating materials was found to give good accuracy for measuring the calorific value of natural gas. In the preparation of a sensor element, the coating can be applied from a solution. Examples of suitable deposition processes for the coatings include dropcasting (deposition by pipette), spincoating (a thin film of the material is created by rapid spinning motion) and printing (automated deposition of droplets, by for example inkjet printing). The coating is then typically cured. These methods are well-known and can provide transducers with a coating layer with the desired thickness.

In yet a further aspect, the invention relates to a gas sensor comprising a sensor array as described and a casing for said sensor array. Typically, the casing encloses the sensor array. The casing can protect the coating and the sensor elements to mechanical damage and may seal any electronics from the fuel gas stream. Often, the casing comprises a chamber in which said sensor elements are exposed and which is provided with at least one opening for a gaseous stream. The casing is typically provided with one or more channels for the gas stream, each channel having an inlet or an outlet, for continuous flow of the gas stream over the coated transducers. For example, the casing may provide a separate channel for different sensor elements. The casing typically comprises means for mounting the sensor to a pipe or tube segment, typically a segment that is provided with a socket for the sensor. The sensor is preferably releasable mounted on a pipe fixture. In a preferred embodiment, the gas sensor is an inline gas sensor comprising a sensor array as described, preferably wherein in said sensor array the transducer of each of said sensor elements comprises a capacitive sensor coated with said coating, and/or preferably a casing comprising a chamber in which said sensor elements are exposed and which is provided with at least one opening for a gaseous stream, wherein said casing is mountable or mounted to, or integrated in, a pipeline segment. Preferably, said sensor is suitable for inline analysis of the composition of a gaseous stream comprising methane and one or more selected from the group consisting of ethane, propane, carbon dioxide and water.

A further preferred application of the sensor array is in a sensor for detecting methane or other gases, for example of leaks from pipelines for gas streams, in particular of methane leakage, for example in gas production. Such a sensor can for example be placed on the outside of a pipeline.

FIG. 1 shows a schematic plan of an example of a sensor array according to the invention. Sensor array 1 on a PCB comprises five sensor elements 2A-2E, each having an exposed surface (in the plan view) and a different coating thereon. The sensor further comprises microprocessor 3 with an integrated memory device 6, and an electric feed 4 and electronic conduits 5 for electronic output signals from each of sensor elements 2A-2E to microprocessor 3, and an outlet 7 for a calculated data signal from microprocessor 3.

Figure 2:
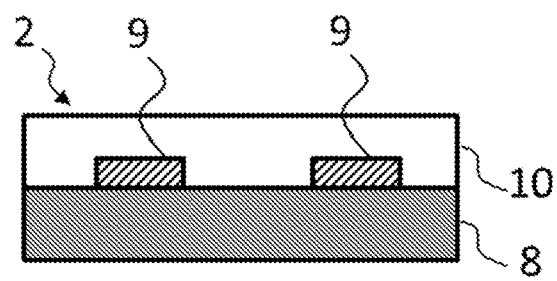

FIG. 2 shows a vertical cross section of a sensor element comprising a substrate 8 and electrodes 9 as transducer (capacitive sensor) end coating 10.

All references cited herein are hereby completely incorporated by reference to the same extent as if each reference were individually and specifically indicated to be incorporated by reference and were set forth in its entirety herein.

The use of the terms "a" and "an" and "the" and similar referents in the context of describing the invention (especially in the context of the claims) are to be construed to cover both the singular and the plural, unless otherwise indicated herein or clearly contradicted by context. The terms "comprising", "having", "including" and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein. Variation of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject-matter recited in the claims appended hereto as permitted by applicable law. Moreover, any combination of the above-described elements in all possible variations thereof is encompassed by the invention unless otherwise indicated herein or otherwise clearly contradicted by context. The claims are to be construed to include alternative embodiments to the extent permitted by the prior art.

For the purpose of clarity and a concise description features are described herein as part of the same or separate embodiments, however, it will be appreciated that the scope of the invention may include embodiments having combinations of all or some of the features described.

The invention will now be further illustrated by the following non-limiting examples.

EXAMPLES

Experiment 1

Quartz Crystal Microbalance experiments were carried out for various quartz crystals. The quartz crystals had an operating frequency of 5 MHz, a diameter of 1 inch and were obtained from Inficon. Coating solutions were prepared by mixing a polymeric matrix (resin) material a solvent and optionally an additive and a few drops of the coating solutions were applied using a spincoater. The coated crystals were heated at 80-90° C. for 1-2 hours for curing of the polymeric matrix.

Table 1 gives the coating compositions. Herein, ratios are in weight/weight. NanoZeo100 is NanoLTA-100, Zeolite LTA (4 Å, Na-form), 100 nm, available from Nanoscape. NanoZeo300 is NanoLTA-300, Zeolite LTA (3 Å, K-form), 300 nm, available from Nanoscape. The cryptophane compound is cryptophane-A.

For coating 1 the solvent was ethanol, for coating 4 IPA, for coatings 6, 7, and 14-19 THF, for coatings 8, 10-12 $CH_2Cl_2$, and for coatings 9 and 13 PCF770.

Experiment 2

Gas uptake characteristics of coated crystals 1-19 as shown in table 1 were measured in a Gas Exposure System with a Teflon flow cell, controlled gas flow and measures the temperature and moisture level. Measurements were performed with an Inficon Research Quartz Crystal Microbalance (QCM) in which the gas uptake is measured by change in mass obtained from a change in the resonance frequency of the crystal.

The signal observed for $N_2$ was the baseline signal. The flow speed with 500 ml/min and the moisture level generally below 1%. Gas stream of a gas component in $N_2$ were used, percentages of the gas component are in vol. %.

Table 1 shows that HPDMS itself absorbs some methane. Comparing crystal 14 with 15 and crystal 17 with 19, a slight increase in methane selectivity is visible upon addition of a small amount of cryptophane. Without wishing to be bound by way of theory, the small amounts of cryptophane may provide a more finely divided morphology and better distribution in the matrix, which increase its accessibility for methane. Upon increase of the cryptophane content (crystals 16 and 18), the sensitivity is reduced.

Table 2 shows methane uptake for crystal 8 as a function of % methane, the methane uptake for crystal 11, and the uptake of $CO_2$ onto crystal 9. $R^2$ is the coefficient of determination of a straight line fit of the data. Compared to crystal 8, the coating is thicker but contains less cryptophane. Nevertheless, crystal 11 has better sensitivity to methane. However, crystal 11 has also a strong mass change upon exposure to e.g. $CO_2$.

TABLE 1

Coating composition for QCM and mass changes upon gas exposure of crystals coated with coatings. [a][b]

| Crystal | Coating | 100% $CH_4$ | 20% $C_2H_6$ | 10% $C_3H_8$ | 100% $CO_2$ | Ratio $CO_2/CH_4$ | Layer thickness [d] |
|---|---|---|---|---|---|---|---|
| 1 | PEI | 0.05 | n.r | n.r. | [c] | | 5.7 |
| 4 | PAAm | 0.1 | n.r. | n.r. | −0.2 | −2.0 | 2.9 |
| 6 | PMDS/NanoZeo100 83/17 | 0.03 | 0.17 | 0.35 | 0.47 | 15.7 | 2.3 |
| 7 | PMDS/NanoZeo300 82/18 | 0.03 | 0.33 | 0.4 | 0.79 | 26.3 | 1.7 |
| 8 | PMDS/Cryptophane 50/50 | 0.06 | 0.15 | 0.6 | 0.38 | 6.3 | 2.0 |
| 9 | Teflon-AF 1600 | −0.02 | 0.08 | 0.22 | 0.57 | −28.5 | 0.63 |
| 11 | PDMS/Cryptophane 87/13 | 0.45 | 1.5 | 2.3 | 4.3 | 9.6 | 4.7 |
| 13 | Teflon/Cryptophane 90/10 | −0.02 | n.d. | n.d. | 0.56 | −28.0 | 0.93 (0.7) |
| 14 | SU-8 | 0.03 | 0.075 | n.r. | 1.1 | 36.7 | 1.1 (1.1) |
| 15 | SU-8/Cryptophane 99/1 | 0.06 | 0.1 | 0.05 | 1.3 | 21.7 | 1.2 |
| 16 | SU-8/Cryptophane 90/10 | 0.05 | 0.15 | 0.1 | 2.5 | 50.0 | 2.2 |
| 17 | HPDMS | 0.11 | 0.25 | 0.57 | 0.82 | 7.5 | 1.9 (1.6) |
| 18 | HPDMS/Cryptophane 95/5 | 0.26 | 0.55 | 10.2 | 10.8 | 60.9 | 3.0 |

TABLE 1-continued

Coating composition for QCM and mass changes upon gas exposure of crystals coated with coatings. [a][b]

| Crystal | Coating | 100% $CH_4$ | 20% $C_2H_6$ | 10% $C_3H_8$ | 100% $CO_2$ | Ratio $CO_2/CH_4$ | Layer thickness [d] |
|---|---|---|---|---|---|---|---|
| 19 | HPDMS/Cryptophane 98/2 | 0.34 | 0.61 | 1.4 | 1.8 | 5.3 | 2.5 |

[a] Data are given in μg/cm² relative to the baseline $N_2$ signal.
[b] N.R. = no response. n.d. = not determined.
[c] No stable signal could be obtained.
[d] Estimation of the layer thickness based on the resonance frequency of the crystal before and after coating. In brackets: direct measurement of the layer thickness on a Dektak apparatus.

TABLE 2

Gas uptake of selected crystals

| Crystal 8 PDMS/Cryptophane 50/50, $CH_4$ | | Crystal 11 PDMS/Cryptophane, 87/13, $CH_4$ | | Crystal 9 Teflon, $CO_2$ | |
|---|---|---|---|---|---|
| % gas | Δm | % gas | Δm | % gas | Δm |
| 20 | 0.032 | 20 | 0.125 | 10 | 0.052 |
| 40 | 0.037 | 60 | 0.269 | 20 | 0.111 |
| 60 | 0.044 | 80 | 0.35 | 30 | 0.169 |
| 80 | 0.042 | 100 | 0.447 | 50 | 0.32 |
| 100 | 0.061 | | | 100 | 0.573 |
| $R^2$ | 0.8221 | $R^2$ | 0.9951 | $R^2$ | 0.9942 |

Experiment 3

Bare comb electrodes obtained from NXP were coated with two coatings. The chip was placed in the Teflon holder of the Gas Exposure System and connected to an LCR analyzer (Iviumstat, Ivium). The change in capacitance was measured upon exposure to $N_2$, $CH_4$ and $CO_2$.

Table 3 shows the results for a coating of HDPMS with 10% w/w cryptophane. The chip 1 was subsequently exposed to air, then to $N_2$, then to $CH_4$ and finally to $CO_2$, each stream 100 vol. %. The difference in capacitance upon each change of gas is shown. Table 3 also shows the change in capacitance for chip 2 which was subsequently exposed to $N_2$, then to $CH_4$, then to $CO_2$, and finally to $N_2$. The difference in capacitance (in pF) upon each change of gas is shown.

TABLE 3

Change in capacitance (pF)

| | 0.1 kHz | 1 kHz | 10 kHz | 100 kHz |
|---|---|---|---|---|
| chip 1 | | | | |
| Air | 0 | 0 | 0 | 0 |
| $N_2$ | −0.85 | −0.57 | −0.40 | 0.26 |
| $CH_4$ | −0.72 | −0.43 | −0.30 | 0.76 |
| $CO_2$ | −0.65 | −0.32 | −0.22 | 0.78 |
| chip 2 | | | | |
| $N_2$ | 0.010 | 0.033 | −0.1 | −0.037 |
| $CH_4$ | 0.074 | 0.085 | 0.22 | 0.049 |
| $CO_2$ | 0.30 | 0.29 | 0.22 | 0.057 |
| $N_2$ | −0.010 | −0.03383 | 0.1 | 0.037 |

A further experiment was carried out for a capacitance sensor coated with SU-8/10 wt. % cryptophane. The loss of water when exposed to dry $N_2$ had a significant influence on the capacitance; in addition equilibration took 30 minutes.

Moreover, the decrease in capacitance upon exposure to $CH_4$ is small and the difference with the $CO_2$ signal was small.

The results can be summarized as follows. Polymeric coatings readily (ab)sorb propane and $CO_2$, but sorb methane and ethane to a much smaller extent. Teflon is particularly sensitive and selective to $CO_2$. PAAm is very sensitive to water and is a promising sensor for detection of the water content of fuel gas streams. Teflon, SU-8 and HPDMS and their mixtures with cryptophane gave better results than PDMS in terms of reproducibility and reliability of the QCM measurements, but have lower sensitivities for methane. In the case of SU-8 and HPDMS, the presence of a small amount of cryptophane (1-2 wt. %) provided in a increase in the methane sensitivity compared to the coatings without cryptophane. Higher amounts of 5-10 wt. % cryptophane surprisingly resulted in a loss of the additional methane sensitivity. Without wishing to be bound by way of theory, this may be due to a change in the morphology of the cryptophane.

Experiment 4

An analysis of table 1 was carried out, based on five sensor elements and four components (methane, ethane, propane and $CO_2$). This provided the Example Sensor Array 1 consisting of five sensor elements as in table 4, with the Δm (mass change) as obtained with the QCM experiments as indicated in the table.

TABLE 4

Example Sensor Array 1

| Coating | Δm for 100% $CH_4$ | Δm for 20% $C_2H_6$ | Δm for 10% $C_3H_8$ | Δm for 100% $CO_2$ | Layer thickness (μm) |
|---|---|---|---|---|---|
| PAAm (a) | 0.1 | n.r. | n.r. | −0.2 | 2.9 |
| Teflon AF 1600 | −0.02 | 0.08 | 0.22 | 0.57 | 0.63 |
| SU-8 | 0.03 | 0.075 | n.r. | 1.1 | 1.1 (1.1) |
| HPDMS | 0.11 | 0.25 | 0.57 | 0.82 | 1.9 (1.6) |
| HPDMS/ Cryptophane 98/2 w/w | 0.34 | 0.61 | 1.4 | 1.8 | 2.5 |

(a) PAAm gave a response of 3 μg/cm² for 4000 ppm water.

Assuming an error of ±0.01 fF for a capacitance sensor in capacity reading for each electrode and of 5 Hz for QCM, multiple regression analysis gives an accuracy for the calorific value (CV) for Example Sensor Array 1 as in table 5. For each gas stream, 50 ppm water was included.

TABLE 5

Accuracy of Example Sensor Array 1

Error in CV for 5 Hz response deviation

| Gas stream | CV [MJ/m³] | HPDMS/ Cryptophane 98/2 | SU-8 | HPDMS | Teflon | PAAm | Total |
|---|---|---|---|---|---|---|---|
| GG | 34.74 | −0.37% | −0.17% | 0.67% | 0.54% | 0.00% | 1.77% |
| BioGas | 25.07 | −0.52% | −0.24% | 0.93% | 0.75% | 0.00% | 2.45% |
| HG | 40.01 | −0.32% | −0.15% | 0.59% | 0.47% | 0.00% | 1.53% |
| FHG | 44.16 | −0.29% | −0.14% | 0.53% | 0.43% | 0.00% | 1.39% |

Error in CV for 0.01 fF response deviation

| Gas stream | CV | HPDMS/ Cryptophane 98/2 | SU-8 | HPDMS | Teflon | PAAm | Total |
|---|---|---|---|---|---|---|---|
| GG | 34.74 | −0.20% | −0.09% | 0.34% | 0.27% | −0.01% | 0.91% |
| BioGas | 25.07 | −0.26% | −0.12% | 0.48% | 0.39% | 0.00% | 1.25% |
| HG | 40.01 | −0.17% | −0.09% | 0.29% | 0.23% | −0.01% | 0.79% |
| FHG | 44.16 | −0.15% | −0.07% | 0.27% | 0.22% | 0.00% | 0.71% |

Example Sensor Array 2 has sensor elements as in table 6, with the Δm (mass change) as obtained with the QCM experiments as indicated in the table.

TABLE 6

Example Sensor Array 2

| Coating | Δm for 100% CH₄ | Δm for 20% C₂H₆ | Δm for 10% C₃H₈ | Δm for 100% CO₂ | Layer thickness (μm) |
|---|---|---|---|---|---|
| PAAm (a) | 0.1 | n.r. | n.r. | −0.2 | 2.9 |
| Teflon-AF 1600 | −0.02 | 0.08 | 0.22 | 0.57 | 0.63 |
| SU-8 | 0.03 | 0.075 | n.r. | 1.1 | 1.1 (1.1) |
| PDMS/ Cryptophane 87/13 w/w | 0.45 | 1.5 | 2.3 | 4.3 | 4.7 |
| HPDMS/ Cryptophane 98/2 w/w | 0.34 | 0.61 | 1.4 | 1.8 | 2.5 |

(a) PAAm gave a response of 3 μg/cm² for 4000 ppm water.

Example Sensor Array 2 has accuracies as indicated in table 7. As can be seen, the error levels on the QCM are now ranging between 0.9% and 1.6% and on the capacitive sensor even below 1%, which meets the desired accuracy.

In the calculations, the used gas compositions GG (Groningen Gas), BioGas, HG (High calorific value gas) and FHG (Future HG) are as in table 8.

TABLE 8

Gas streams (volume concentration [%])

| | GG | HG | FHG | Biogas |
|---|---|---|---|---|
| CH₄ | 81.30 | 91.4 | 80.3 | 60 |
| C₂H₆ | 2.85 | 3.0 | 11.7 | 0 |
| C₃H₈ | 0.37 | 1.5 | 3.9 | 0 |
| C₄H₁₀ | 0.14 | 0.5 | 0 | 0 |
| C₅H₁₂ | 0.04 | 0.1 | 0 | 0 |
| C₆H₁₄ | 0.05 | 0 | 0 | 0 |
| N₂ | 14.35 | 2.0 | 4.1 | 0 |
| O₂ | 0.01 | 0 | 0 | 0 |
| CO₂ | 0.89 | 1.5 | 0 | 35 |
| Other (NH₃, H₂O, HS) | 0 | 0 | 0 | 5 |
| Density (1 bar, 273 K) [kg/m³] | 0.831 | 0.795 | 0.865 | 1.172 |
| Calorific Value [MJ/m³] | 34.95 | 40.70 | 44.16 | 23.88 |
| Calorific Value [MJ/kg] | 42.08 | 51.20 | 51.08 | 20.37 |

TABLE 7

Accuracy of Example Sensor Array 2

| Gas stream | CV [MJ/m³] | HPDMS/ Cryptophane 98/2 | SU-8 | PDMS/ Cryptophane 87/13 | Teflon | PAAm | Total |
|---|---|---|---|---|---|---|---|

Error in CV for 5 Hz response deviation

| GG | 34.74 | −0.16% | −0.20% | 0.02% | 0.77% | 0.00% | 1.15% |
| BioGas | 25.07 | −0.22% | −0.28% | 0.02% | 1.06% | 0.00% | 1.59% |
| HG | 40.01 | −0.14% | −0.17% | 0.02% | 0.67% | 0.00% | 1.00% |
| FHG | 44.16 | −0.13% | −0.16% | 0.01% | 0.60% | 0.00% | 0.90% |

Error in CV for 0.01 fF response deviation

| GG | 34.74 | −0.09% | −0.11% | 0.00% | 0.39% | −0.01% | 0.59% |
| BioGas | 25.07 | −0.12% | −0.14% | 0.01% | 0.54% | 0.00% | 0.82% |
| HG | 40.01 | −0.08% | −0.10% | 0.00% | 0.33% | −0.01% | 0.52% |
| FHG | 44.16 | −0.07% | −0.08% | 0.01% | 0.31% | 0.00% | 0.46% |

Experiment 5

A set of nine coatings was tested for sensitivity to gas exposure, by measuring the capacitance changes of coated electrodes. Nine bare comb electrodes obtained from NXP were coated with different coatings according to table 9. Each of these coated chips were subsequently placed in a Teflon gas flowcell of the Gas Exposure System and connected to an LCR analyzer (Iviumstat, Ivium). The gas flowcell contains a holder for NXP test chips, a temperature sensor and an in- and outlet for a gas stream. The measurements were done at room temperature; the temperature was not controlled. In order to monitor the relative humidity of the gas stream, a second flow cell, containing a moisture sensor, was connected to the exit stream of the first cell. The moisture level was kept to a minimum by flushing the entire system with $N_2$ gas for up to 16 hours, prior to each measurement. The change in capacitance was measured upon exposure to continuous flows of 500 ml/min 100% $CH_4$, 250 ml/min 20% $C_2H_6$ (in $N_2$), 500 ml/min 10% $C_3H_8$ (in $N_2$), 500 ml/min 100% $CO_2$, and 500 ml/min 5% relative humidity (in $N_2$). The capacitance was measured at 16 different frequencies, ranging from 100 Hz to 100 000 Hz. The measurement at 720 Hz was used for determining the capacitance changes as the noise level was lowest at this frequency. For each coating, the capacitance at 1 bara of $N_2$ was regarded as the baseline signal. In all cases, the observed capacitance change upon exposure to a gas was determined with respect to the baseline signal. In table 9, the nominal capacitance values of the uncoated chips, as well as the capacitance values of the chips after coating and at exposure to 1 bara of $N_2$ (i.e. the baseline value) are listed. In table 10, the capacitance changes upon gas exposure are given as absolute values and in table 11 as percentages of the baseline signal.

For all data presented in tables 10 and 11, the observed capacitance change upon exposure to a gas was determined with respect to exposure to pure $N_2$ gas. To enable analysis of natural gas in which $N_2$ is present, the response of the chips to $N_2$ gas with respect to vacuum was determined by extrapolation from the response to $N_2$ at various pressures. A high-pressure gas exposure chamber was used which was integrated into the Gas Exposure System. The capacitance was measured at 2, 3 and 6 bara and the capacitance changes were determined relative to the baseline signal at 1 bara. The responses to 1 bara $N_2$ with respect to vacuum were then determined by extrapolation and are given in table 12.

TABLE 9

Nominal capacitance values for the chips, before and after coating

| Chip # | Coating | C (uncoated) (pF) | C (coated) (at 1 bara N2) (pF) |
|---|---|---|---|
| 1 | SU-8 | 31.0 | 54.9 |
| 2 | Teflon | 30.0 | 35.9 |
| 3 | PDMS | 30.2 | 45.8 |
| 4 | PDMS/Cryptophane (50/50) | 29.5 | 48.3 |
| 5 | PDMS/MOF Z1200 (50/50) | 30.0 | 42.7 |
| 6 | PDMS/Zeolite NH4 CZP200 (MFI) (50/50) | 30.8 | 46.3 |
| 7 | PDMS/Cryptophane (83/17) | 41.8 | 69.7 |
| 8 | HPDMS/Cryptophane (98/2) | 31.1 | 42.6 |
| 9 | HPDMS | 30.9 | 43.9 |

TABLE 10

Absolute capacitance changes upon gas exposure.

| | | ΔC (pF) (absolute value) | | | | |
|---|---|---|---|---|---|---|
| Chip # | Coating | 100% $CH_4$ | 20% $C_2H_6$ | 10% $C_3H_8$ | 100% $CO_2$ | 5% RH |
| 1 | SU-8 | n.r. | 0.014 | 0.030 | 0.17 | 0.88 |
| 2 | Teflon | n.r. | 0.016 | 0.033 | 0.037 | n.r. |
| 3 | PDMS | n.r. | −0.013 | n.r. | −0.027 | 0.018 (6% RH) |
| 4 | PDMS/Cryptophane (50/50) | 0.11 | 0.014 | n.r. | 0.16 | 0.24 |
| 5 | PDMS/MOFZ1200 (50/50) | 0.013 | 0.025 | 0.094 | 0.037 | 0.028 |
| 6 | PDMS/Zeolite NH4CZP200 (MFI) (50/50) | 0.022 | −0.36 | −0.44 | 0.22 | 2.87 |
| 7 | PDMS/Cryptophane (83/17) | 0.11 | n.r. | −0.0096 | 0.19 | 0.30 |
| 8 | HPDMS/Cryptophane (98/2) | 0.033 | 0.021 | n.r. | 0.16 | n.m. |
| 9 | HPDMS | −0.0067 | −0.0095 | −0.027 | −0.016 | n.r. | n.r. = no response.
n.m. = not measured.

TABLE 11

Capacitance changes upon gas exposure, as percentages of the $N_2$ baseline signal.

| | | ΔC (pF) (percentage of baseline value) | | | | |
|---|---|---|---|---|---|---|
| Chip # | Coating | 100% $CH_4$ | 20% $C_2H_6$ | 10% $C_3H_8$ | 100% $CO_2$ | 5% RH |
| 1 | SU-8 | n.r. | 0.025 | 0.060 | 0.31 | 1.6 |
| 2 | Teflon | n.r. | 0.044 | 0.093 | 0.10 | n.r. |
| 3 | PDMS | n.r. | −0.028 | n.r. | −0.058 | 0.038 (6% RH) |
| 4 | PDMS/Cryptophane (50/50) | 0.23 | 0.030 | n.r. | 0.33 | 0.49 |
| 5 | PDMS/MOFZ1200 (50/50) | 0.029 | 0.059 | 0.22 | 0.086 | 0.067 |
| 6 | PDMS/Zeolite NH4CZP200 (MFI) (50/50) | 0.048 | −0.76 | −0.96 | 0.48 | 6.20 |
| 7 | PDMS/Cryptophane (83/17) | 0.16 | n.r. | −0.014 | 0.28 | 0.43 |
| 8 | HPDMS/Cryptophane (98/2) | 0.077 | 0.048 | n.r. | 0.35 | n.m. |
| 9 | HPDMS | −0.015 | −0.022 | −0.061 | −0.036 | n.r. | n.r. = no response.
n.m. = not measured.

TABLE 12

Capacitance change for exposure to 1 bara of $N_2$, with respect to vacuum, as determined by extrapolation.

| Chip # | Coating | Response to 1 bara $N_2$ ΔC (pF) |
|---|---|---|
| 1 | SU-8 | 0.098 |
| 2 | Teflon | 0.005 |
| 3 | PDMS | 0.001 |
| 4 | PDMS/Cryptophane (50/50) | 0.018 |
| 5 | PDMS/MOFZ1200 (50/50) | 0.005 |
| 6 | PDMS/Zeolite NH4CZP200 (MFI) (50/50) | 0.251 |
| 7 | PDMS/Cryptophane (83/17) | 0.033 |
| 8 | HPDMS/Cryptophane (98/2) | 0.019 |
| 9 | HPDMS | −0.007 |

Coating Selection for Sensor Array

Out of the nine tested coatings (tables 9-12), six were selected for a gas sensor array. Coating selection was based on the following considerations: (1) The number of coatings should be minimal, but sufficient for estimating partial pressures of the 5 object gases; (2) The standard deviation of the Caloric Value (CV) should be as small as possible. Based on these criteria, the following 6 coatings were selected:

1) SU-8; 2) Teflon; 3) PDMS; 4) PDMS/Cryptophane (50/50); 5) PDMS/MOF Z1200 (50/50); 6) PDMS/Zeolite NH4CZP200 (MFI) (50/50)

CV and its standard deviation ($\sigma_{CV}$) were estimated as follows. The CV is estimated from the partial pressures $p_j$ of the object gases j=1-5 and the $p_j$ values are estimated from the capacity changes $\Delta C_i$ of coating i=1-6 via the experimentally obtained response matrix $\partial C_i/\partial p_j$. From this response matrix and the standard deviation of the capacity measurements ($\sigma_i$=5 fF for the present experiments), we can obtain the covariance matrix $R_{jj'}$ of the estimated partial pressures, from which $\sigma_{CV}$ follows. Table 13 contains the CV for all 5 object gases and table 8 the CV for a number of typical gas mixtures. Table 14 contains $\sigma_{CV}$ for 4 different cases. Rows 1 and 2 are computed for the response matrix with $N_2$ background. Row 1 contains $\sigma_{CV}$ for all 9 coatings, giving a best CV accuracy of 7.18 MJ/m³ for any selection of 6 coatings. For the above selection of 6 coatings, we obtain 8.27 MJ/m³, the value of row 2. In the possible presence of other gases besides the object gases, one should rather work with vacuum background. For that purpose, we subtracted the $N_2$ background from the response matrix using our measurements of pure $N_2$ responses for all coatings. Rows 3 and 4 contain $\sigma_{CV}$ for vacuum background, giving a lower bound of the CV accuracy of 7.47 MJ/m³ for 9 coatings and 8.41 MJ/m³ for the selected 6 coatings. Note that these values are based on the estimated capacity accuracy of 5 fF. It is expected that in actual operational conditions, capacity measurements will be considerably more accurate, giving more accurate CV estimations. $\sigma_{CV}$ of 8.41 MJ/m³ amounts to a relative accuracy of about 19-35% of the CV of the different gas mixtures of table 8.

TABLE 13

Caloric Values of object gases

| | $CH_4$ | $C_2H_6$ | $C_3H_8$ | $CO_2$ | $H_2O$ |
|---|---|---|---|---|---|
| CV [MJ/m³] | 39.79 | 70.58 | 101.20 | 0 | 0 |

TABLE 14

Standard deviation CV for a coating standard deviation of 5 fF.

| | Case | $\sigma_{CV}$ [MJ/m³] |
|---|---|---|
| 1 | All 9 coatings, $N_2$ background | 7.18 |
| 2 | Selected 6 coatings, $N_2$ background | 8.27 |
| 3 | All 9 coatings, vacuum background | 7.47 |
| 4 | Selected 6 coatings, vacuum background | 8.41 |

Experiment 6

A gas sensor array was constructed, consisting of the six coated chips mentioned in the previous experiment. A gas measuring chamber containing all the six chips was used. The array of chips was analyzed using a LCR analyzer and a multiplexer. With this setup, all six chips were simultaneously exposed to gas mixtures and all analyzed at the same time. In order to establish the relationship between gas concentration and response for each chip and each gas, a series of measurements was carried out using the sensor array at different concentrations of each gas. Furthermore, several gas mixtures mimicking the natural gas types mentioned in Table 8 were measured as well. With the measured responses of the six individual chips, the gas composition and its CV can be calculated according to the method described in experiment 5. Table 15 shows a selected number of measured responses for the gas sensor array.

TABLE 15

Capacitance measurements ($\Delta C$, pF, 720 Hz) with the gas sensor array containing six chips.

| | Chip # | | | | | |
|---|---|---|---|---|---|---|
| Gas | 1 | 2 | 3 | 4 | 5 | 6 |
| $CH_4$ | n.r. | 0.006 | 0.003 | 0.101 | 0.009 | −0.182 |
| $CH_4$:$N_2$ = 75:25 | n.r. | 0.004 | −0.005 | 0.099 | 0.006 | −0.134 |
| $CH_4$:$N_2$ = 50:50 | n.r. | 0.007 | n.r. | 0.068 | 0.004 | −0.074 |
| $CH_4$:$C_2H_6$:$N_2$ = 80:10:10 | n.r. | 0.012 | −0.011 | 0.110 | 0.017 | −0.216 |
| $CH_4$:$C_3H_8$:$N_2$ = 80:5:15 | 0.030 | 0.033 | −0.005 | 0.077 | 0.043 | −0.075 |
| $CH_4$:$C_2H_6$:$C_3H_8$:$N_2$ = 75:10:5:10 | 0.019 | 0.035 | −0.015 | 0.084 | 0.051 | −0.103 | n.r. = no response.

The invention claimed is:

1. A method for analysing the composition of a gaseous mixture, comprising at least two gaseous components, one of which is methane, the method comprising
contacting the gaseous mixture with a sensor, wherein the sensor comprises a sensor array comprising at least two sensor elements, wherein each of said sensor elements comprises a transducer coated with a coating comprising a polymeric material having at least one property that is responsive to one or more of said gaseous components when exposed thereto, wherein said sensor elements differ at least in the composition of the coating,
providing an energy input to said transducers that is converted to output signals based on said property, and
obtaining said output signals, wherein optionally said output signals are data signals,
wherein the method is for determining the calorific value of the gaseous mixture.

2. The method of claim 1, wherein the gaseous mixture comprises ethane and/or propane and wherein the coating of at least one sensor element comprises a compound with selectivity for absorption of methane over ethane, and the coating of at least one other sensor element comprises a compound with selectivity for absorption of ethane and/or propane over methane.

3. The method of claim 1, wherein said gaseous mixture is a gaseous stream, wherein the method is for determining the calorific value of said gaseous stream, and comprises passing the gaseous stream over the sensor elements.

4. The method of claim 1, wherein said gaseous stream is a stream of natural gas or biogas or a mixture comprising natural gas and/or biogas.

5. The method of claim 1, further comprising:
providing said data signals to a computer processor which is in communication with a computer memory device in which instructions are stored for conversion of said data signals to an estimated composition parameter, and
calculating in said processor said estimated composition parameter using said instructions and said data signals from said different sensor elements.

6. The method of claim 5, wherein said estimated composition parameter is the calorific value of said gaseous mixture.

7. The method of claim 5, wherein said estimated composition parameter is the methane concentration.

8. The method of claim 1, wherein said gaseous mixture comprises at least one component selected from the group consisting of ethane, propane, carbon dioxide and water.

9. The method of claim 1, wherein said gaseous mixture is a gaseous stream, the method comprising removing non-gaseous contaminations from the gas stream prior to contacting the gas stream with the sensor.

10. The method of claim 1, wherein said transducers are a capacitive sensor and wherein said responsive property of said polymeric material is the relative permittivity.

11. The method of claim 1, wherein said gaseous mixture is a gaseous stream, wherein the method is a method of in-line analysis of the composition of the gaseous stream and wherein the sensor is an in-line device mountable or mounted to, or integrated in a pipeline segment or flow meter, and wherein the step of contacting the gaseous stream with said sensor comprises flowing at least part of the gaseous stream over the sensor array.

12. The method of claim 1, wherein the sensor array comprises
a first sensor element comprising a coating comprising cured epoxy resin,
a second element sensor comprising a coating comprising a fluoropolymer,
a third sensor element comprising a polymeric organosilicon compound, and
wherein said sensors are different from each other, and wherein the coating of at least one sensor element of the sensor array comprises a molecular encapsulation material in a polymeric matrix, wherein said encapsulation material is selected from the group consisting of cryptophane, zeolite and metal-organic framework.

13. A sensor array, comprising at least two sensor elements, wherein each of said sensor elements comprises a transducer coated with a coating comprising a polymeric material having at least one property that is responsive to one or more gaseous components when exposed thereto, wherein said sensor elements differ at least in the composition of the coating,
wherein the coating of at least one sensor element comprises a compound with selectivity for absorption of methane over ethane, and the coating of at least one other sensor element comprises a compound with selectivity for absorption of ethane and/or propane over methane.

14. The sensor array of claim 13, wherein said transducer is configured for converting an energy input to a data signal based on said property, preferably wherein said transducers are capacitive sensors.

15. The sensor array of claim 14, comprising:
a first sensor element comprising a coating comprising poly(allylamine), or a coating comprising a polymer and metal organic framework or zeolite,
a second sensor element comprising a coating comprising a homopolymer or copolymer of tetrafluoroethylene,
a third sensor element comprising a coating comprising cured polyepoxide SU-8 resin giving a polymer comprising bisphenol-A diglicydyl ether residues, a fourth sensor element comprising a coating comprising polydimethylsiloxane and a cryptophane compound, and a fifth sensor element comprising a coating comprising polydimethylsiloxane, optionally a sixth sensor element comprising a coating comprising a polymer and zeolite, wherein each of said sensor elements has a capacitive sensors as transducer.

16. The sensor array of claim 13, wherein at least one sensor element has a coating comprising a cryptophane compound and/or one or more polymers selected from the group consisting of a polymer comprising repeating units comprising an amine group, a fluoropolymer, a polymeric organosilicon compound, a polyisoprene, a polymer of intrinsic microporosity, and cured epoxy resin.

17. The sensor array of claim 13, wherein at least one sensor has a coating comprising one or more polymers selected from the group consisting of:

a fluoropolymer selected from the group consisting of polymers and copolymers of tetrafluoroethylene, and polymers and copolymers of vinylidene fluoride, a polymeric organosilicon compound selected from the group consisting of polydimethylsiloxane, polydiethylsiloxane, polydiphenylsiloxane, and copolymers of any of these polymers, and an amine comprising polymer selected from the group consisting of polyallylamine, polyvinylamine, polyethyleneimine, and copolymers of any of these polymers, a cured epoxy resin selected from cured cycloaliphatic epoxides and aromatic epoxides.

18. The sensor array of claim 13, comprising the combination of:

a first sensor element comprising a coating comprising a zeolite, a metal organic framework, and/or a polymer comprising repeating units comprising an amine group, a second element sensor comprising a coating comprising a fluoropolymer, a third sensor element comprising a polymeric organosilicon compound, wherein said sensor elements are different from each other, and wherein the coating of at least one sensor element of the sensor array comprises a cryptophane compound in a polymeric matrix.

19. The sensor array of claim 18, wherein the sensor array further comprises a fourth sensor element comprising a coating comprising a cured epoxy resin comprising a cross-linked polymer comprising aromatic rings, and a fifth sensor element comprising said cryptophane compound in a polymeric matrix, and optionally a sixth sensor element comprising a coating comprising a zeolite or a metal organic framework.

20. An inline gas sensor comprising the sensor array of claim 13, wherein in said sensor array the transducer of each of said sensor elements comprises a capacitive sensor coated with said coating, and comprising a casing comprising a chamber in which said sensor elements are exposed and which is provided with at least one opening for a gaseous stream, wherein said casing is mountable or mounted to or integrated in a pipeline segment.

21. A sensor array comprising at least two sensor elements, wherein each of said sensor elements comprises a transducer coated with a coating comprising a polymeric material having at least one property that is responsive to one or more gaseous components when exposed thereto, wherein said sensor elements differ at least in the composition of the coating, wherein at least one sensor element has a coating comprising a cryptophane compound and/or one or more polymers selected from the group consisting of a polymer comprising repeating units comprising an amine group, a fluoropolymer, a polymeric organosilicon compound, a polyisoprene, a polymer of intrinsic microporosity, and cured epoxy resin.

* * * * *